United States Patent [19]

Bringham et al.

[11] Patent Number: 4,698,207
[45] Date of Patent: Oct. 6, 1987

[54] INTEGRATED MEMBRANE OXYGENATOR, HEAT EXCHANGER AND RESERVOIR

[75] Inventors: Richard L. Bringham, San Clemente; Lucas S. Gordon, Laguna Beach; Karl E. Mosch, Irvine, all of Calif.

[73] Assignee: Baxter Travenol Laboratories, Inc., Deerfield, Ill.

[21] Appl. No.: 885,207

[22] Filed: Jul. 14, 1986

[51] Int. Cl.⁴ .............................................. A61M 1/16
[52] U.S. Cl. .............................. 422/46; 210/321.72; 128/DIG. 3; 422/48
[58] Field of Search ............................ 210/321.2, 321.4; 422/45-48; 128/DIG. 3

[56] References Cited

U.S. PATENT DOCUMENTS

| | | |
|---|---|---|
| 3,677,800 | 7/1972 | Wright . |
| 3,717,502 | 2/1973 | Masuhara et al. . |
| 4,087,567 | 5/1978 | Sullivan . |
| 4,111,659 | 9/1978 | Bowley ................................ 422/48 |
| 4,151,088 | 4/1979 | Wolf, Jr. et al. . |
| 4,158,693 | 6/1979 | Reed et al. . |
| 4,180,896 | 1/1980 | Reed et al. . |
| 4,282,180 | 8/1981 | Raible . |
| 4,297,318 | 10/1981 | Raible . |
| 4,331,697 | 5/1982 | Kudo et al. . |
| 4,336,224 | 6/1982 | Siposs . |
| 4,374,088 | 2/1983 | Stenberg et al. . |
| 4,376,095 | 3/1983 | Hasegawa . |
| 4,424,190 | 1/1984 | Mather, III et al. . |
| 4,440,723 | 4/1984 | Gordon . |
| 4,451,562 | 5/1984 | Elgas et al. . |
| 4,490,331 | 12/1984 | Steg, Jr. . |
| 4,529,614 | 7/1985 | Burns . |

Primary Examiner—Michael S. Marcus
Attorney, Agent, or Firm—Bernard, Rothwell & Brown

[57] ABSTRACT

A membrane oxygenator includes an upper nested arrangement of a hard shell venous reservoir, a bowl-like defoamer within the reservoir and a heat exchanger coil vertically supported within the defoamer, and includes a membrane oxygenator unit mounted on the bottom of the upper arrangement. The oxygenator unit includes an inlet chamber with a tangential inlet providing swirling blood flow to dislodge air bubbles and centrifuge air to an upper center region of an inlet chamber where gas is exhausted through a vent. A bottom blood outlet chamber of the blood oxygenator unit has a relatively thin vertical cross-sectional area such that priming flow velocity therein discharges all air from the outlet chamber.

6 Claims, 9 Drawing Figures

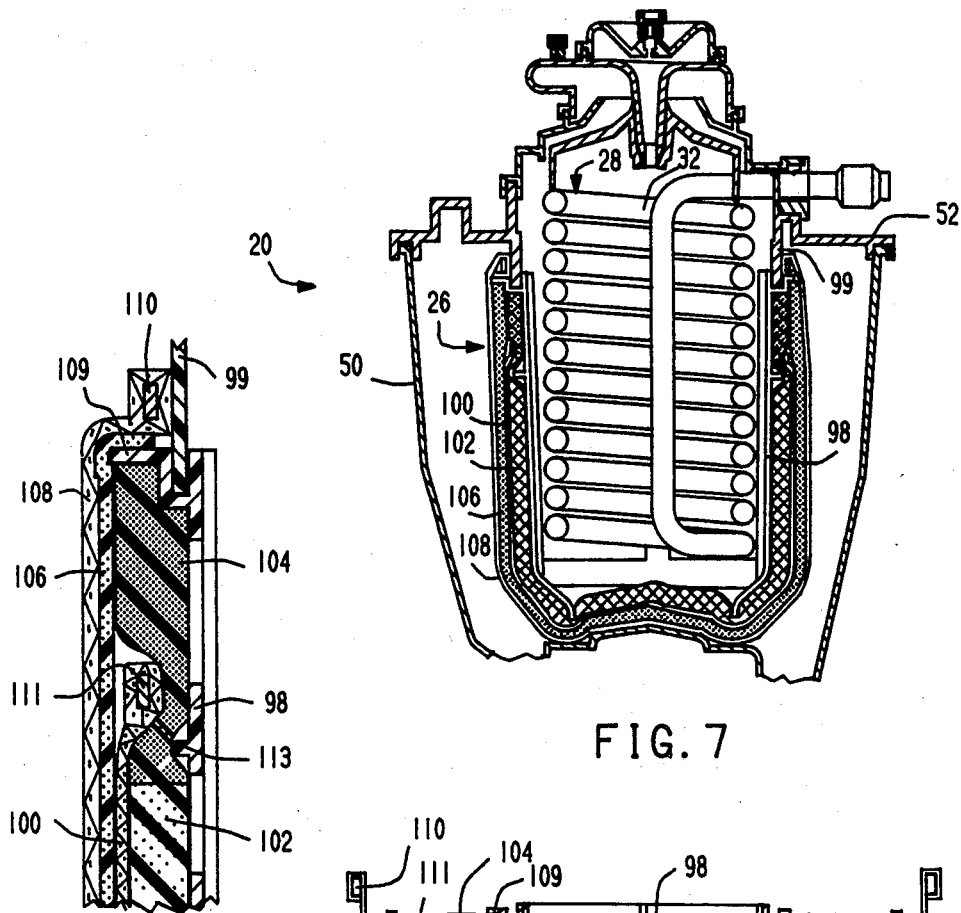
FIG. 7
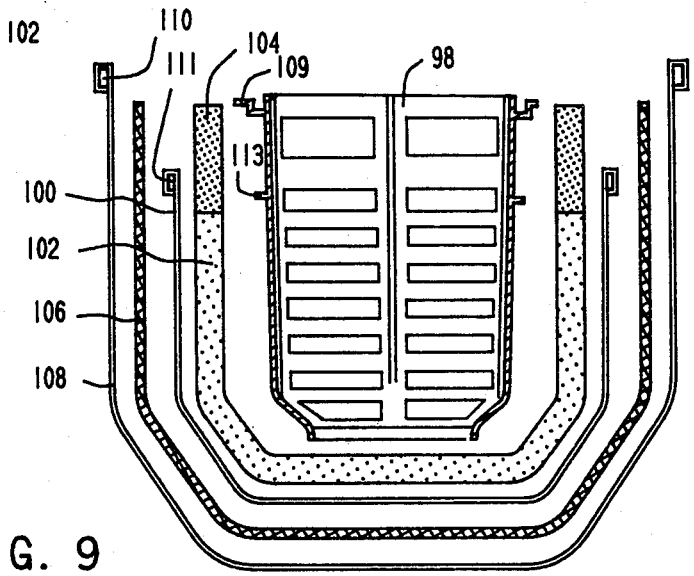
FIG. 8
FIG. 9

INTEGRATED MEMBRANE OXYGENATOR, HEAT EXCHANGER AND RESERVOIR

TECHNICAL FIELD

The invention relates to apparatus for oxygenating blood, and particularly to oxygenators employing gas-permeable, liquid-impermeable membranes.

DESCRIPTION OF THE PRIOR ART

The prior art, as exemplified in U.S. Pat. No. 4,151,088 U.S. Pat. No. 4,376,095, U.S. Pat. No. 4,424,190 and U.S. Pat. No. 4,451,562, includes a number of blood oxygenators employing a gas-permeable membrane through which oxygen passes from an oxygen-rich gas stream to a bloodstream and through which carbon dioxide passes from the blood to the gas stream. The oxygenators and associated pumps are used in surgical procedures, such as open-heart surgery, to temporarily replace the normal lung and heart functions. Generally, the oxygenator includes a reservoir, along with a heat exchanger, in the extracorporeal circulating circuit. The reservoir provides for fluctuation in the quantity of blood being received from the patient's body while the heat exchanger is used to maintain proper blood temperature and to make up for heat loss to the ambient through the tubing and other parts of the extracorporeal circuit. Several of the prior art oxygenators combine the reservoir, heat exchanger and membrane gas exchange device into an integral unit so that blood flow may proceed successively through the reservoir, heat exchanger and oxygenator section. In one type of prior art oxygenator, the reservoir, heat exchanger and membrane oxygenator sections are in a linear vertical arrangement with the reservoir on top so that gas bubbles in the blood flow to the unit are collected by buoyancy at the top of the reservoir where the gas can be removed through a vent. However, this linear arrangement results in a vertically elongated unit where the blood inlet is at an elevation near to the elevation of the patient rendering gravity flow of venous blood from the patient to the oxygenator less efficient than apparatus arrangements having blood inlets at a lower elevation. Additionally, the prior art apparatus generally requires large priming volumes in order to remove all air from the heat exchanger and membrane oxygenator sections, and these sections must be maintained full during operation to avoid generating and passing gas bubbles back to the patient in the oxygenated blood flow; for example, air can be trapped beneath heat exchanger coils during filling, and if not prevented by priming and maintaining the coil section full, air bubbles can be generated by the trapped air and passed to the patient. Arrangements where the various sections are mounted side-by-side, rather than being in a vertical arrangement, further complicate the priming since such sections tend to form traps for air to resist air removal during priming.

The prior art also contains bubbler-type oxygenators, as exemplified in U.S. Pat. Nos. 4,282,180, 4,297,318, 4,336,224, 4,374,088 and 4,440,723, wherein oxygen is introduced as bubbles into blood to oxygenate the blood and drive off carbon dioxide. In these oxygenators, the bubbling or foaming mixture must be passed through a defoamer, which is generally a porous urethane foam or woven screen structure to filter bubbles from the blood. One type of prior art bubbling apparatus provided for compactness in design by employing an outer shell forming the reservoir and containing a similar shaped defoamer which in turn had a heat exchanger coil mounted within the upper interior portion thereof. The air bubbling facility is located at the top to generate a blood-air mixture which is passed downward over the heat exchanger coils to be received within the defoamer. After passing through the defoamer, the oxygenated blood passes through an outlet in the lower portion of the shell for return to the patient. The turbulent nature of the bubbling or foaming of the blood makes this type of oxygenator more stressful on the blood compared to membrane-type oxygenators, such as hollow membrane fiber oxygenators, where efficient gas exchange occurs through the gas permeable membrane.

Generally defoamers are not utilized in closed system membrane-type oxygenators since there is no bubble mixture or foam which must be removed, and the addition of a defoamer unit would further increase the overall length of the apparatus. Further, the inclusion of a defoamer section can require additional priming and blood volumes.

SUMMARY OF THE INVENTION

In one aspect, the invention is summarized in a blood oxygenator including a nested combination with a hard shell reservoir within which is contained a defoamer which in turn contains a heat exchanger coil with blood inlet facilities for providing blood flow cascading over the heat exchanger coil. A membrane oxygenator unit is mounted on the bottom of the reservoir housing.

In a second aspect of the invention, a membrane blood oxygenator unit has a blood inlet facility mounted on the upper end of a tubular housing wherein the inlet facility includes a cylindrical inlet chamber with an inlet for directing incoming blood tangentially to produce circular flow such that gas bubbles are dislodged from edges of the inlet chamber and are urged by buoyancy and centrifugal forces to an upper center region where a vent is provided for discharging gas from the inlet chamber. Gas permeable and liquid impermeable membrane facilities are mounted within the tubular housing to form separate blood and gas flow paths wherein the blood flow path communicates with the inlet chamber and a lower outlet.

In a third aspect of the invention, a thin outlet chamber, collecting blood from outlet ends of hollow membrane fibers, has a vertical cross-section area selected relatively small so as to maintain a blood flow velocity fast enough to discharge all air therefrom during priming, but slow enough to avoid blood cell trauma. The hollow membrane fibers, having lumens forming a blood flow path from the upper blood inlet chamber to the lower thin outlet chamber, are mounted at respective upper and lower ends in upper and lower seals closing the respective upper and lower ends of a tubular housing to form a gas exchange chamber through which the fibers extend.

An object of the invention is to integrate a membrane blood oxygenator, a heat exchanger and a hard shell reservoir into one integral unit that provides high performance levels of oxygenation and heat exchange, yet has a low priming volume and is easy to set up and debubble.

Another object of the invention is to construct a membrane blood oxygenator which is compact and short to save space in an operating room and allow placement of the inlet closer to the floor for better drainage from the patient.

It is a further object of the invention to construct a membrane blood oxygenator with reduced risk of generating and passing gas bubbles to a patient.

One advantage of the invention is that a nested arrangement of a heat exchange coil inside a defoamer which is inside a molded hard shell reservoir mounted on the top of an oxygenator module provides a compact design with low priming volume. Providing inlet blood flow to cascade over the heat exchange coil enables operation with low volume in the reservoir since bubbles in the incoming blood or generated during passage over the heat exchanger are removed by the defoamer. Feeding of the blood flow to the upper end of the heat exchanger coil provides efficient heat exchange at both low and high reservoir levels; at a low level, a film-like cascading flow over the heat exchanger coils provides full heat exchange, and at higher levels, the heater coil is at least partially immersed to provide the same efficient heat exchange.

Another advantage of the invention is provided by an inlet chamber to the membrane oxygenator unit wherein blood flow is introduced tangentially to provide for circular flow. The circular flow within the inlet chamber dislodges any air bubbles, and the buoyancy and centrifugal forces on the bubbles tend to drive these bubbles to the upper center portion of the chamber where air is withdrawn through a vent. Further, the vent can remove air which is pumped into the inlet chamber should the reservoir run dry during pumping to prevent injection of air in a patient.

Still another advantage of the invention, results from the provision of a narrow or thin outlet chamber with a small vertical cross-section so as to generate rapid blood flow therethrough sufficient to remove air while avoiding blood cell trauma. Further, this is achieved with a generally downward blood flow which, in prior art designs, was unable to remove air from large outlet chambers.

Other objects, advantages and features of the invention will be apparent from the following description of the preferred embodiment taken in conjunction with the accompanying drawings wherein:

BRIEF DESCRIPTION OF THE DRAWINGS

FIG. 7 is an elevational section view of a modified heat exchanger, defoamer and hard shell reservoir arrangement which may be substituted in the unit of FIG. 1.

FIG. 8 is a cross-section view of a broken-away of a defoamer assembly in the arrangement of FIG. 7.

FIG. 9 is an exploded assembly view of the defoamer assembly of the arrangement of FIG. 7.

DESCRIPTION OF THE PREFERRED EMBODIMENTS

Figure 1:
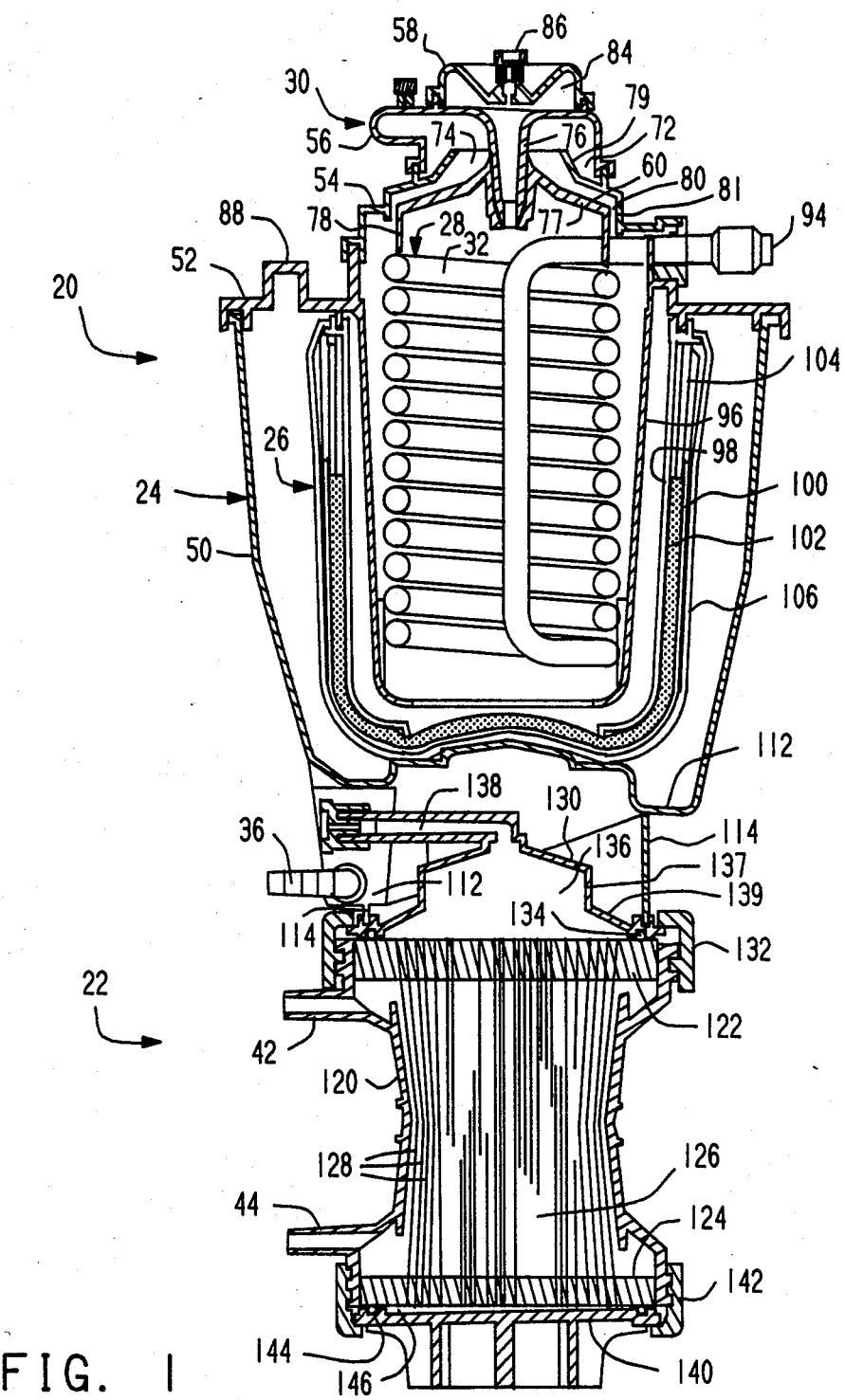
FIG. 1 is a sectional elevation view of an integrated membrane oxygenator, heat exchanger and reservoir constructed in accordance with the invention.

As shown in FIG. 1, one embodiment of a blood oxygenator in accordance with the invention includes an upper unit indicated generally at 20 mounted on a lower unit indicated generally at 22. The upper unit 20 includes a nested arrangement of an outer hard shell reservoir or housing 24, a defoamer indicated generally at 26 and a vertical heat exchanger coil indicated generally at 28. A blood inlet facility indicated generally at 30 is mounted on top of the upper unit 20 for directing incoming blood flow to the upper convolution 32 of the heat exchanger coil 28. The lower unit 22 is a membrane-type oxygenation unit.

Figure 5:
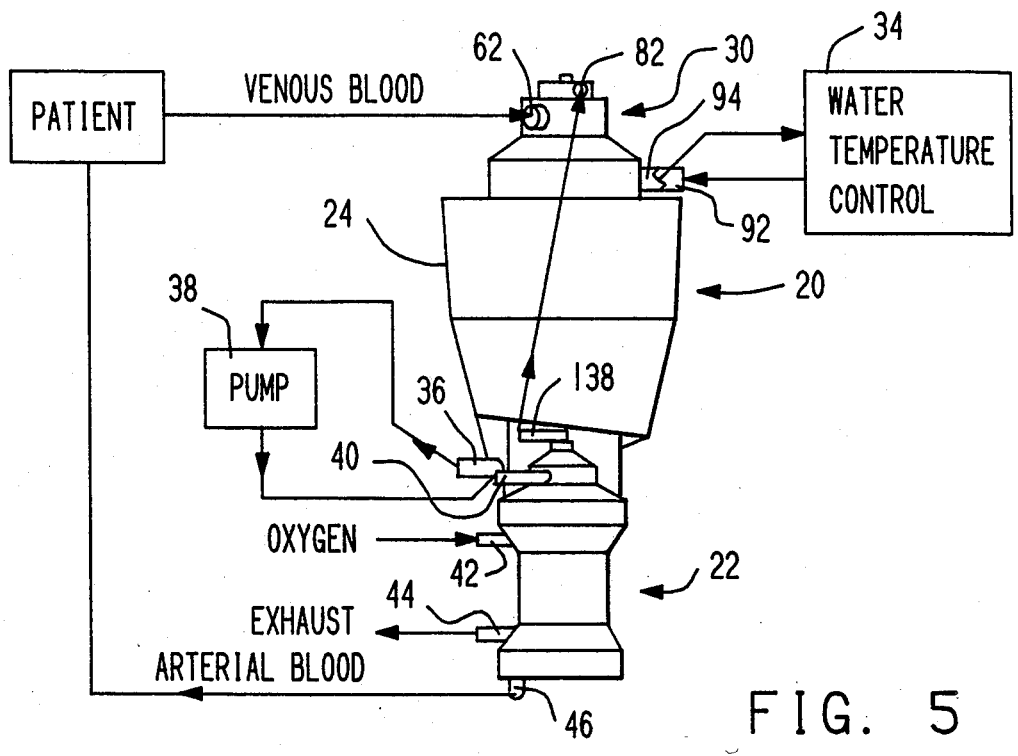
FIG. 5 is a schematic illustration of a typical arrangement employing the membrane oxygenation unit of FIG. 1.

In a typical employment of the blood oxygenator as shown in FIG. 5, venous blood from a patient is passed to the inlet facility 30, while water supplied by a conventional water temperature control 34 is passed through the heat exchanger coil to provide for warming of the incoming blood. After passing through the defoamer, the blood is withdrawn from the reservoir 24 at outlet 36 by a conventional pump 38 which then applies the blood to an inlet 40 of the lower oxygenator unit 22. Within the unit 22 the blood passes through a blood flow path determined by a gas-permeable and liquid-impermeable membrane. Oxygen-rich gas from a conventional source is applied through inlet 42 to the gas flow path defined by the membrane to reoxygenate the blood. The excess oxygen together with carbon dioxide passing through the membrane from the blood is exhausted through gas outlet 44. The reoxygenated blood is then fed through outlet 46 from unit 22 back to the patient.

Referring back to FIG. 1, the reservoir 24 includes a molded thermoplastic, bowl-shaped container portion 50 and a cover formed by molded thermoplastic parts 52, 54, 56, 58 and 60. The parts 52, 54, 56, 58 and 60 are secured together by conventional means such as by being induction thermally bonded together utilizing a commerical iron-containing bonding agent. Alternative bonding techniques such as solvent bonding, adhesive bonding, RF bonding, ultrasonic bonding, vibration bonding, etc., may be used. The parts 52, 54, 56 and 58 have mating peripheral tongue and groove arrangements formed thereon to enhance strength and sealing of the bonds. The part 52 is shown mounted on the housing 50 using a rotating seal of the type disclosed in U.S. Pat. No. 4,440,723 so that the relative orientation of the upper assembly can be adjusted relative to the housing 50; however, a fixed joint may be used instead of the rotating seal.

Figure 2:
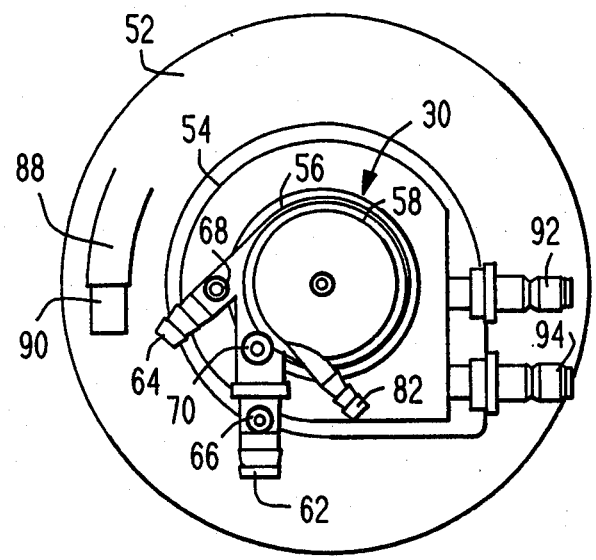
FIG. 2 is a top view of the integrated unit of FIG. 1.

As shown in FIG. 2, the blood inlet portion 30 is formed by part 56 which has tangential venous inlet connector 62 and tangential cardotomy inlet connector 64. Venous sampling ports 66 and 68 are provided on the connectors 62 and 64, and a venous temperature probe 70 is provided on the connector 62. The inlets 62 and 64 open tangentially into an inlet chamber 72, FIG. 1, which communicates with a bottom annular opening 74 defined by parts 54 and 60. The part 60 is mounted on a center projection 76 extending downward from the top of part 56, and has a downwardly and outwardly flaring skirt portion 77 which at the upper end defines the inner edge of the annular opening 74. As more particularly disclosed in U.S. patent application Ser. No.

565,236, filed Dec. 27, 1983, the skirt portion 77 terminates in a vertical downwardly or cylindrical portion 78 which extends to the top center of the surface of the tube forming the first convolution 32 of the coil 28. The part 54 has an inner upward flaring flange 79 defining the outer edge of the annular opening 74, and extends outwardly and downwardly to a vertical cylindrical portion 81 which cooperates with the vertical cylindrical portion 78 of the member 60 for forming a narrow annular opening 80, approximately 0.050 inch (1.3 mm.) wide, to provide a film-like flow which will follow the downward extending cylindrical portion 78 of member 60 to the top convolution 32 of the coil 28.

As an alternative to the skirt distribution for the incoming bloodflow, a plate (not shown) with a circle of holes disposed over the top coil convolution could be employed.

The upper member 58 includes a further auxiliary venous blood inlet connector 82, FIG. 2, which is tangential with chamber 84, FIG. 1. The chamber 84 opens at the bottom end through projection 76 into the center of the heating coil 28. An auxiliary venous port 86 is formed in the center of the member 58.

The cover part 52 is provided with a raised portion 88 in which is mounted a venous reservoir gas vent 90 for providing an exhaust from the reservoir to remove gas which is carried or evolves from the blood flow input.

The heat exchanger coil 28 is a coiled, smooth aluminum heat exchanger tube which has respective inlet and outlet sections 92 and 94 secured by appropriate mating openings in the parts 52, 54 and 60. The outer surface of the aluminum coil 28 is preferably anodized and/or coated with a commercial urethane-based biocoat. Alternatively, the coil 28 may be stainless-steel, convoluted, bellowed, fluted, or otherwise formed with an extended surface. The coil coating is optional or may be an epoxy or other thin coating of biocompatible material applied by a suitable technique such as electrostatic powder coating.

The cover part 52 of the embodiment cf FIG. 1 includes a downward extending support 96 for retaining the coil centrally within the upper unit 20. In a further preferred embodiment illustrated in FIGS. 7-9, the support member 96 of FIG. 1 is eliminated and the coil 28 is retained by a cylindrical grid structure 98 utilized to support the defoamer 26 centrally within the unit 20. The grid structure 98 is mounted at its upper end on a downward extending cylindrical lip 99 of the cover part 52. The heat exchanger coil 28 has no inner wall and only minimal support from the outer support 96, FIG. 1, or grid 98, FIG. 5, to hold it vertically. The coil 28 is positioned in the upper member 20 with all of its convolutions 32 arranged vertically for enabling the film-like blood flow to cascade downward over the convolutions.

As shown in FIGS. 7, 8 and 9, one preferred blood/-gas separation system or defoamer 26, which is described in more detail in U.S. patent application Ser. No. 885,963, filed on even date herewith, for "Liquid and Gas Separation System" by Lucas S. Gordon, includes a cup-shaped screen member 100 interposed between the lower portion of inner and outer cup-shaped porous members 102 and 106. The members 100, 102 and 106 are contained within a sock 108 secured at its upper end to the lip 99 by a nylon cable tie 110 above an upper flange 109 of the grid 98 to secure the defoamer on the cylindrical grid 98. The screen 100, which is made of a suitable biocompatible plastic material such as woven polyester having a pore size in the range 40-100 microns, preferably 50 microns, extends about three-fourths of the height of the defoamer and is secured by a nylon cable tie 111 just above a flange 113 on the grid 98. The screen can be coated with a heparin complex. The members 102 and 106 are preferably open-celled polyurethane but could alternately be polypropylene woven mesh or some other large pore, large surface area materials. The inner member 102, having a thickness of about one-half inch (1.3 cm.), has a pore size in the general range of 20 to 120 pores per inch, preferably in the range of 80 to 110 pores per inch, and especially preferred, of about 100 pores per inch. The upper portion 104, approximately upper one-fourth as shown by the heavier stippling, of member 102 is coated with a conventional silicone antifoam compound. The outer member 106, having a thickness of about one-eighth inch (0.3 cm.), has a pore size preferably in the range from 15 to 25 pores per inch and especially preferred of about 15 pores per inch. The sock 108 can be, for example, a knit sock having a pore size in the range of 40 to 500 microns, preferably, a knit sock of polyester material with a pore size of approximately 200 microns.

The venous reservoir 50 is designed to hold sufficiently large volumes of blood to handle normal fluctuations in flow returning from the patient. The bottom of the reservoir 50 is formed with an inclined surface 112, FIG. 1, leading to the outlet connector 36 for enabling substantially all of the blood to be drained from the reservoir. Flanges 114 extending downward from the reservoir 50 are suitably secured in mating grooves of the lower oxygenation module 22 to form the two units into an integral structure.

The oxygenation unit 22 includes a molded vertical tubular housing 120 and upper and lower seals 122 and 124 closing the respective upper and lower ends of the tubular housing 120 to form a chamber 126 for receiving oxygen from inlet connector 42 in the housing 120 and discharging gas through the gas outlet 44 formed in the housing 120. A multiplicity of hollow membrane fibers 128 extend through the chamber 126 and have upper ends secured in the seal 122 and lower ends secured in the seal 124 with the ends of the hollow fibers being open to the outside of the respective seals 122 and 124. The seals 122 and 124 are formed from a suitable fiber sealant such as polyurethane adhesive. The hollow fibers are conventional polypropylene, polyethylene or other hydrophobic microporous plastic or silicone fibers. The number and size of the hollow membrane fibers are selected to handle the normal blood flow of the patient with a minimum pressure drop. For fibers having an internal diameter of about 200 microns and an outside diameter of approximately 250 microns with a wall pore size within the range from about 0.01 to 0.2 microns, the number of fibers is in the range from 10,000 to 100,000. For example, a pediatric unit for handling blood flow, which in a pediatric patient can be 3 liters per minute, has about 41,000 hollow fibers, and an adult unit, for handling up to 7 liters of blood flow per minute, has 71,000 hollow fibers.

Figure 3:
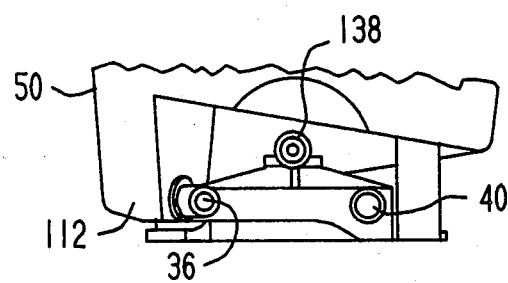
FIG. 3 is an elevation view, taken from the left side, of a broken away middle portion of the oxygenation unit of FIG. 1.

A molded cap 130 is secured on the upper end of the tubular housing 120 by a retaining ring 132 with a silicone O-ring 134 sealing the peripheral of the cap against the seal 122. The cap 130 forms a blood inlet chamber 136 into which the blood inlet 40, FIGS. 3 and 5, opens. A vent port 138 is formed at the highest point in the center top of the cap 130. The cap 130 has a generally vertical cylindrical center portion 137 and a bottom portion 139 which flares outward and downward from the cylindrical center portion so as to distribute the blood flow over the flat upper surface of the seal 122 and the openings of the hollow fibers 128 therein. The inlet 40 opens tangentially along a horizontal plane into the cylindrical center portion 137. The diameter of the cylindrical portion 137 is selected, relative to the incoming flow, small enough to produce a swirling blood velocity in chamber 136 sufficient to dislodge air bubbles formed at the outer edges of the chamber, but large enough to avoid forming a vortex which exposes the open upper ends of the membrane fibers in the center to air or gas in the upper portion of the chamber 136. Additionally, the diameter of portion 137 is selected to generate centrifugal forces in the blood swirl in chamber 136 sufficient to substantially assist the normal gas buoyancy to cause any gas bubbles in the blood to rise to the top center.

Figure 4:
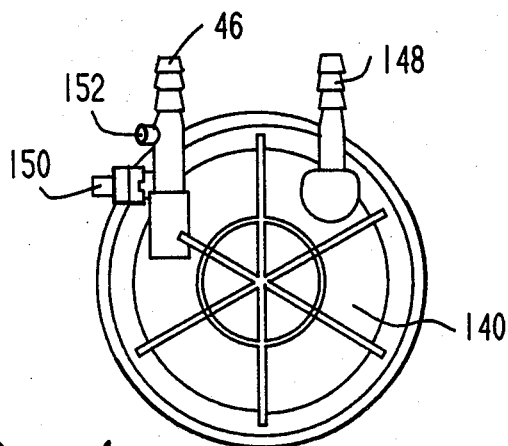
FIG. 4 is a bottom view of the oxygenation unit of FIG. 1.

An outlet cap 140 is secured on the bottom end of the tubular housing 120 by a retaining ring 142 with a silicone O-ring 144 sealing the periphery of the cap 140 against the outer periphery of the flat lower surface of the seal 124. The cap 140 forms an outlet chamber 146 which is relatively thin or narrow in vertical dimension and tapers from about 0 vertical thickness at the right side in FIG. 1 to about 0.1 inch (2.5 mm.) at the left side. The main blood outlet 46, FIG. 4, is mounted on the cap 140 and opens into the largest portion of the chamber 146 on the left side. The outlet chamber 146 is formed relatively thin to produce a relatively high velocity in priming or blood flow, but below a velocity which would induce stress in the blood, to easily dislodge air during priming and maintain the outlet chamber 146 free of gas. Generally, the cross-section of the chamber 146 taken along a vertical plane which bisects the chamber 146, as shown in FIG. 1, has a cross-sectional area which is in the range from about 0.5 to 2.0 times the cross-sectional area of the inside diameter of the outlet 46. An auxiliary arterial outlet connector 148 is also mounted on the bottom cap 140 in communication with the outlet chamber 146. A temperature probe 150 and a vent with a luer cap 152 are formed on the outlet connector 46.

The various molded plastic parts, such as the reservoir shell 50, cover parts 52, 54, 56, 58 and 60, tubular housing 120, upper and lower caps 130 and 140 and the retaining rings 132 and 142 are made from a clear polymer material such as polycarbonate, acrylic, ABS, SAN, etc. Where appropriate, various parts, such as the receptacle shell 50, cover parts 52, 54, 56, 58 and 60, caps 130 and 140, membrane fibers 128, seals 122 and 124, etc., may be coated with a conventional antithrombogenic material to avoid forming clots in the blood being processed.

In priming of the oxygenator, priming fluid, such as the patient's blood or other compatible fluid is fed into the inlet facility, for example, through main inlet connector 62 or through any other of the inlet connectors 64, 82 or ports 66, 68 and 86. The priming fluid after cascading down the heating coils 28 or being poured directly through the inlet 76 into the center, passes through the defoamer 26 and into the bottom of the reservoir 50 where the priming fluid is fed through connector 36 to the pump 38. When the pump 38 is primed the priming fluid then passes into inlet connector 40 into the inlet chamber 136 of the oxygenation module 22. Air will be exhausted from the chamber 136 through vent 138 which, for example, may be connected to inlet connector 82 to pass any gas flow back into the center of the defoaming cup such that air within the unit 20 is discharged through the air port 90. The swirling of the fluid produced in chamber 130 by the tangential inlet quickly dislodges trapped air bubbles at the peripheral portions of the cap 130 and, due to buoyancy and centrifugal forces, moves the dislodged air bubbles into the upper center region of the chamber 136 for discharge through vent 138. Fluid in chamber 136 passes through the lumens of the hollow membrane fibers 128 into the outlet chamber 146. With the chamber 146 having a relatively small volume, the incoming fluid flow through the hollow fibers 128 rapidly displaces all of the air, driving air out of the blood outlet 46. The initial flow of output fluid may be either passed back into the inlet facility 30 of the upper member 20 or otherwise utilized or discarded as may be appropriate. Then the oxygenator is connected for normal operation.

The present oxygenator requires a relatively small amount of priming fluid compared to existing membrane-type blood oxygenators. Air bubbles including small entrained air bubbles in the incoming priming fluid are removed initially by the defoamer 26. After the pump 38 is primed the construction of the oxygenator 22 enables rapid and efficient discharge of air from the blood flow passage therethrough without requiring a large volume flow of priming fluid. Since the pressure within the chamber 136 will be greater than the pressure within the upper unit 20, air, dislodged by the swirling movement and carried to the top center by buoyance and the centrifugal forces on the priming fluid within the chamber 136, will be withdrawn from the chamber 136 through vent 138 and into the upper unit 24 to insure that air is rapidly removed from the chamber 136 to avoid the chance of being incorporated in bubbles passing to a patient.

In normal operation of the blood oxygenator, the venous blood flow is applied through the main blood inlet 62 into chamber 72 where the swirling of the incoming blood created by the tangential entry results in even distribution of the blood around the annular opening 74. Blood flow follows the skirt 70 and is evenly dispensed through the narrow opening into a film-like flow directed to the top center of the tube forming the first convolution 32 of the coil 28. This film-like flow then follows the convolutions of the coils 28 downward, cascading from one convolution to the next, until the blood reaches the pool of blood in the reservoir or flows from the bottom convolution.

The reservoir does not have to be full, or the coil 28 does not have to be immersed in order to provide for efficient heating of the blood flow. When the reservoir level is low, the film-like flow over the outer surfaces of the coil convolutions produces efficient heating of the blood, and when the reservoir is high, heating is performed by the film flow over the upper convolutions as well as by the immersion of the lower convolutions in the pool of blood.

The blood must pass through the defoamer 26 to reach the outlet 36 of the reservoir. Thus, any bubbles which are created by lowering and raising the level of blood on the coils, i.e., air trapped between convolutions can generate bubbles, is effectively removed.

Normal blood flow occurs through the lower portion of the defoamer which does not contain the silicone coating to thus avoid possible inclusion of the coating material in the blood returning to the patient. In the event of increased Gaseous contents in the incoming blood flow, the blood foam height can reach the upper portion 104 of the defoamer where the silicone coating effectively speeds up the removal of air bubbles from the blood.

The design of the cap 130 and inlet chamber 136 with the tangential entrance of blood flow, in addition to providing forces which supplement the buoyancy of any air bubbles which may have been introduced into the blood in order to collect the air bubbles at the center topmost portion of the chamber 136, provides safety in the event that the reservoir 24 runs dry. With the pressure in the chamber 136 being greater, due to the pump 38, than in the unit 24, gas will be discharged through vent 138 back into the unit 24. In the event that the reservoir 24 runs dry and the pump 38 begins pumping air into the chamber 136, all of the air can be expelled from the chamber 136 through the vent 138 to avoid pumping air to the patient.

Figure 6:
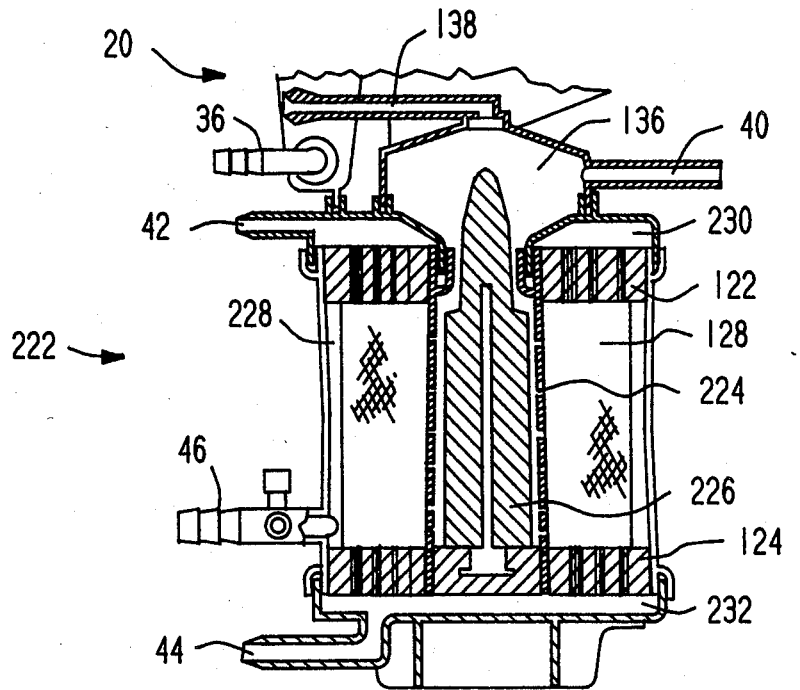
FIG. 6 is an elevational section view of a modified membrane section suitable for employment in the unit of FIG. 1.

In FIG. 6, there is shown a modified oxygenator unit 222 which may be an alternative for the unit 22 of FIG. 1. In the unit 222, the gas flow passes through the lumens of the hollow fibers 128 and the blood flow is around the outside of the membrane fibers. In this embodiment the hollow fibers 128 are wound or positioned in an annulus, with upper and lower ends of the fibers secured in the seals 122 and 124, about a perforated center tube 224 into which the blood inlet chamber 136 opens. A distributor member 226 is mounted within the tube 224 for directing the blood flow outward through the perforated tube 224 and space between fibers 128 into an annular space 228 outside of the annular fiber mat 128 where the blood flow then proceeds to blood outlet 46 which communicates with the bottom of chamber 228. Oxygen is emitted through oxygen inlet 42 into upper gas chamber 230 where the oxygen enters the lumens of the hollow fibers 128 and passes therethrough to the bottom chamber 232 from which the gas is exhausted through gas outlet 44.

The above embodiment has the oxygenator unit 22 or 222 mounted on the bottom of the upper reservoir unit 20. These units 22 and 20, or 222 and 20, could be independent and unattached.

Other incoming blood flow arrangements are also possible. The blood inlet flow could flow into the top, down a tube (not shown) to the bottom of the heat exchanger, up over the heat exchanger and spill over into the defoamer. The blood inlet could also go directly into the bottom of the reservoir housing, through the defoamer, up over the heat exchanger coil and spill over into the defoamer.

Many modifications, variations and changes in detail may be made to the above-described embodiments without departing from the scope and spirit of the invention as defined in the following claims.

What is claimed is:

1. A blood oxygenator comprising
    an upper bowl-like housing having a bottom with blood outlet means and a top with blood inlet means,
    said upper housing forming a receptacle for accumulating varying amounts of venous blood,
    a heat exchanger coil mounted within the housing and having a plurality vertically arranged convolutions,
    said upper housing inlet means including means for directing incoming blood flow over the convolutions of the heat exchanger coil,
    a defoamer mounted within the upper housing and interposed between the heat exchanger and the upper housing outlet to remove air bubbles in the blood passing to the upper housing outlet,
    a lower housing mounted on the bottom of the upper housing,
    gas-permeable, liquid-impermeable membrane means mounted in the lower housing and forming separate blood and gas flow paths, and
    said lower housing having blood inlet means and blood outlet means communicating with respective opposite ends of the blood flow path, and having gas inlet means and gas outlet means communicating with respective opposite ends of the gas flow path.

2. A blood oxygenator as claimed in claim 1 wherein the gas-permeable and liquid-impermeable membrane means includes a plurality of hollow membrane fibers providing at least a portion of one of the blood flow path or gas flow path through lumens of the hollow fibers and means providing the other path around the outsides of the membrane fibers.

3. A blood oxygenator as claimed in claim 1 wherein the lower housing includes a tubular member having a vertical axis, and upper and lower caps secured on respective upper and lower ends of the tubular housing and defining respective blood inlet and outlet chambers; and wherein the gas-permeable and liquid-impermeable membrane means includes a plurality of hollow membrane fibers extending vertically within the housing, and upper and lower seals closing the upper and lower ends of the cylindrical housing and securing the hollow membrane fibers adjacent to their respective ends such that upper ends of the hollow membrane fibers open into the inlet chamber formed by the upper cap and lower ends of the membrane fibers open into the outlet chamber defined by the lower cap.

4. A blood oxygenator as claimed in claim 1 wherein the lower housing includes a tubular member having a vertical axis, the blood inlet means is mounted on the upper end of the tubular housing and includes a cylindrical inlet chamber with a vertical axis and means for directing incoming blood in a horizontal stream tangentially into the inlet chamber to produce circular flow of the blood in the inlet chamber such that gas bubbles are dislodged from edges of the inlet chamber and are urged by buoyancy and centrifugal forces to an upper center region of the inlet chamber; and said blood oxygenator includes vent means communicating with the upper center region of the inlet chamber for discharging gas.

5. A blood oxygenator as claimed in claim 3 wherein the outlet chamber has a vertical cross-sectional area selected to maintain a blood flow velocity fast enough to discharge all air from the outlet chamber during priming but slow enough to avoid blood cell trauma.

6. A blood oxygenator as claimed in claim 5 wherein the blood outlet means includes a blood outlet connector, and the vertical cross-sectional area of the outlet chamber taken in a vertical plane bisecting the outlet chamber is in the range from about 0.5 to 2.0 times a cross-sectional area of an inside diameter of the outlet connector.

* * * * *